United States Patent [19]

Berkowitz

[11] 4,103,088

[45] Jul. 25, 1978

[54] FORMATION OF CRYSTALLINE [(MONO-TRICHLORO) TETRA-(MONOPOTASSIUM DICHLORO)] PENTA-ISOCYANURATE

[75] Inventor: Sidney Berkowitz, Highland Park, N.J.

[73] Assignee: FMC Corporation, Philadelphia, Pa.

[21] Appl. No.: 721,296

[22] Filed: Sep. 8, 1976

[51] Int. Cl.$^2$ .......................................... C07D 251/36
[52] U.S. Cl. ................................................ 544/190
[58] Field of Search .................... 260/248 C; 544/190

[56] References Cited

U.S. PATENT DOCUMENTS

| | | | |
|---|---|---|---|
| 2,956,056 | 10/1960 | Christian | 260/248 |
| 3,350,317 | 10/1967 | Symes | 260/248 |
| 3,888,856 | 6/1975 | Wojtowicz | 544/190 |
| 4,007,182 | 2/1977 | Wojtowicz | 260/248 |

*Primary Examiner*—John M. Ford

[57] ABSTRACT

Preparing a crystalline [(mono-trichloro) tetra(-monopotassium dichloro)] penta-isocyanurate by reacting an unsubstituted or amino substituted triazine with at least stoichiometric amounts of potassium hypochlorite in an aqueous medium at a temperature of 35° to 70° C and at a pH value of 3.2 to 5.7 for less than about five minutes.

10 Claims, No Drawings

FORMATION OF CRYSTALLINE [(MONO-TRICHLORO) TETRA-(MONOPOTASSIUM DICHLORO)] PENTA-ISOCYANURATE

This invention relates to the formation of crystalline [(mono-trichloro) tetra-(monopotassium dichloro)] pentaisocyanurate by reacting an amino substituted triazine with potassium hypochlorite in an aqueous medium.

Cyanuric acid is commonly represented as existing in two tautomeric forms as follows:

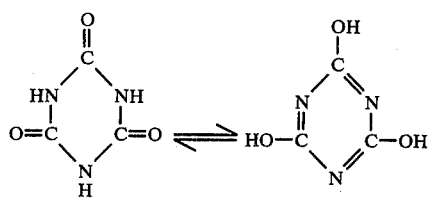

The terms dichloroisocyanuric acid and dichloroisocyanurate refer to the acid and salt respectively in either tautomeric form.

Cyanuric acid is the main product produced by heating urea, biuret or mixtures thereof in a kiln at temperatures of about 200° to 350° C. Unfortunately, the product produced is only composed of about 80% cyanuric acid with the remainder of the product comprising amino substituted triazine impurities. The amino substituted triazine impurities generally contain about 25% ammelide and minor amounts of other impurities such as ammeline, melamine, ammeline:ammelide complex, and cyanuric acid:melamine complex. This cyanuric acid product mixture is conventionally referred to as crude cyanuric acid. Since it is quite difficult to separate the crude cyanuric acid into its component parts to recover pure cyanuric acid, various methods have been proposed to purify crude cyanuric acid by converting the triazine impurities into cyanuric acid by acid hydrolysis. This conversion is sometimes referred to as the acid digestion process.

The acid digestion process comprises mixing crude cyanuric acid with a strong mineral acid to make a slurry containing 10% to 15% undissolved solids. The mineral acids disclosed as being operative are sulfuric, hydrochloric, nitric and phosphoric acid, with sulfuric acid being preferred. The slurry is digested at reflux temperatures (about 104° C) or at higher temperatures while under pressure. These digestion processes result in hydrolysis of most of the triazine impurities to cyanuric acid. Methods employing this procedure are described in U.S. Pat. Nos. 2,768,167, 2,943,088 and 3,107,244.

The use of mineral acid reactions, however, results in partial hydrolysis of the cyanuric acid to ammonia and carbon dioxide, thus decreasing cyanuric acid yields. The formation of a purified cyanuric acid, however, is essential for an efficient conversion of the cyanuric acid into chloroisocyanuric acids and their salts, preferably sodium, lithium or potassium salts, by known processes employed in the prior art.

Dichloroisocyanuric acid and trichloroisocyanuric acid have been produced by mixing purified cyanuric acid with sodium hydroxide and then chlorinating by the addition of chlorine. Specifically, dichloroisocyanuric acid has been produced by mixing cyanuric acid and sodium hydroxide in a mole ratio of 1:2 and then chlorinating the mixture by the addition of chlorine, usually in two stages, until the pH value is between 1.7 and 3.5. This process requires long hold-up times for the chlorination reaction to approach completion and therefore the reactors must be relatively large to obtain sufficient hold-up times and yields.

U.S. Pat. No. 3,035,056 discloses a process for producing sodium dichloroisocyanurate by chlorinating 1 mole of trisodium cyanurate with 2 moles of trichloroisocyanuric acid. Such a reaction is not advantageous since it requires a separate source of trichloroisocyanuric acid to obtain the required reactant for the process.

U.S. Pat. Nos. 3,712,891 discloses another process for producing chloroisocyanuric acids by reacting purified cyanuric acid and hypochlorous acid in an aqueous medium at a temperature of 0° to 50° C. The mole ratio of cyanuric acid to hypochlorous acid is preselected to yield a product having the desired degree of chlorination, that is, a mole ratio of cyanuric acid to hypochlorous acid of 1:2 produces dichloroisocyanuric acid, whereas a molar ratio of cyanuric acid to hypochlorous acid of 1:3 produces trichloroisocyanuric acid.

In contrast, potassium-containing chloroisocyanurate complexes such as [(mono-trichloro) tetra-(monopotassium dichloro)] penta-isocyanurate and mixtures thereof have been produced by reacting potassium dichloroisocyanurate and trichloroisocyanuric acid in an aqueous solvent system at carefully controlled pH values and reactant ratios as described in U.S. Pat. Nos. 3,272,813. This reaction, however, requires separate sources of potassium dichloroisocyanurate and trichloroisocyanuric acid as reactants and extensive purification procedures to remove the solvent system from the product complexes.

It has been unexpectedly discovered that [(mono-trichloro) tetra-(monopotassium dichloro)] penta-isocyanurate and mixtures thereof can be produced directly from unsubstituted or amino substituted triazines without the need for an acid hydrolysis step to purify the crude cyanuric acid, and without the need for separate sources of potassium dichloroisocyanurate and trichloroisocyanuric acid, by reacting an unsubstituted or amino substituted triazine with at least stoichiometric amounts of potassium hypochlorite in an auqeous medium at a temperature of 35° to 70° C and at a pH value of 3.2 to 5.7 for less than about five minutes to completely N-chlorinate all of the available sites on the triazine molecule that can be N-chlorinated and to remove any N, N-dichloro exocyclic nitrogens; cooling the reaction medium to precipitate [(mono-trichloro) tetra(monopotassium dichloro)] penta-isocyanurate; and recovering crystalline [(mono-trichloro) tetra-(monopotassium dichloro)] penta-isocyanurate.

The process of the invention permits the formation of crystalline [(mono-trichloro) tetra-(monopotassium dichloro)] pentaisocyanurate and mixtures containing the same, such as complex mixtures of [(mono-trichloro) tetra-(monopotassium dichloro)] penta-isocyanurate and (mono-trichloro) (monopotassium dichloro) di-isocyanurate, from unsubstituted or amino substituted triazines in a commerically simple and efficient manner without the concommitant metal corrosion problems associated with the prior art acid digestion processes, without the need for large expensive acid digestor reactors, and without the long hold-up times required for the prior art chlorination reactions to approach completion to prepare potassium dichloroisocyanurate and trichloroisocyanuric acid. It also permits recovery of a crystalline product in exceptionally high yields and exceptionally high purities in relatively short periods of time, that is below about 5 minutes.

In the process of the invention, an amino substituted triazine, such as melamine, ammeline, ammelide, ammeline: ammelide complex and cyanuric acid: melamine complex or mixtures thereof is mixed with a sufficient amount of potassium hypochlorite to completely N-chlorinate all of the available sites on the triazine molecule that can be N-chlorinated and to, remove any N, N-dichloro exocyclic nitrogens. Alternatively, purified cyanuric acid or crude cyanuric acid containing ammelide and other amino substituted triazine impurities is mixed with potassium hypochlorite and treated according to the process of the invention to likewise completely N-chlorinate all of the available sites on the triazine molecule that can be N-chlorinated and to remove any N, N-dichloro exocyclic nitrogens. The phrase "amino substituted triazines" as used herein, refers to the specific amino substituted triazines enunciated above as well as to crude cyanuric acid.

The unsubstituted or amino substituted triazines are employed in amounts sufficient to produce a triazine slurry in the aqueous reaction medium. The unsubstituted or amino substituted triazine slurry concentration is not critical. From a commercial process standpoint, however, slurry concentrations from 3 to 20 weight % of the triazine based on the weight of the reaction solution are desirable. Slurry concentrations below about 3 weight % are not economical in view of the small amounts of material being treated. Slurry concentrations above about 20 weight % are difficult to handle and accordingly are not advisable. Preferably, the slurry concentration is between 6 and 14 weight % based upon the weight of the reaction solution.

The unsubstituted or amino substituted triazine slurry is obtained by either mixing dry unsubstituted or amino substituted triazine and potassium hypochlorite in water or mixing aqueous solutions of one or both of these materials together.

To achieve complete conversion of the unsubstituted or amino substituted triazine to [(mono-trichloro) tetra-(monopotassium dichloro)] penta-isocyanurate triazine, at least stoichiometric amounts of potassium hypochlorite must be employed to completely N-chlorinate all of the available sites on the triazine molecule that can be N-chlorinated and to remove any N, N-dichloro exocyclic nitrogens. These amounts will vary with the particular triazine employed and the desired potassium-containing chloroisocyanurate complex product.

Under desirable temperature and pH conditions, [(mono-trichloro) tetra-(monopotassium dichloro)] pentaisocyanurate, commonly referred to as Compound I and mixtures containing the same is produced when the mole ratio of potassium hypochlorite to melamine is 11.2:1, the mole ratio of potassium hypochlorite to ammeline is 8.2:1, the mole ratio of potassium hypochlorite to ammelide is 5.2:1, or the mole ratio of potassium hypochlorite to cyanuric acid is 2.2:1. The mole ratio of potassium hypochlorite to either the amino substituted triazine complexes or to crude cyanuric acid is determined from the aforementioned stoichiometry based upon the specific amino substituted triazines which are present.

Any stoichiometry substantially less than that stated results in the undesirable production of mixtures containing chlorinated amino substituted triazines and/or chlorinated isocyanuric acids and/or their salts. Preferably, potassium hypochlorite is employed in amounts of at least 10% above the stoichiometric amount necessary to completely N-chlorinate all of the available sites on the triazine molecule that can be N-chlorinated and to remove any N, N-dichloro exocyclic nitrogens, and most preferably in amounts of 15% to 30% above the stoichiometric amount.

The stoichiometric reaction results in the formation of 1 mole of nitrogen trichloride for each exocyclic amino group from each triazine molecule. The nitrogen trichloride formed during the reaction may be removed by conventional procedures, such as by sparging the reaction medium with an inert gas and removing the sparged nitrogen trichloride as a waste stream. Other well known procedures for removing nitrogen trichloride from a reaction medium may likewise be employed, which procedures do not constitute a part of this invention.

Conversion of the unsubstituted or amino substituted triazines into potassium-containing chloroisocyanurate complexes is effected at pH values from 3.2 to 5.7 and at temperatures from 35° to 70° C. Higher or lower pH values should not be employed since these result in the formation of potassium dichloroisocyanurate and/or trichloroisocyanuric acid. Higher or lower temperatures should not be employed since these increase triazine ring rupture, thus decreasing product yield.

Maximum conversion of the unsubstituted or amino substituted triazines into [(mono-trichloro) tetra-(monopotassium dichloro)] penta-isocyanurate is achieved at pH values of 4.0 to 5.5 and at temperatures of 45° to 60° C, and preferably at a pH value maintained between 4.7 and 5.0. Maximum conversion of the unsubstituted or amino substituted triazines into mixtures of [(mono-trichloro) tetra-(monopotassium dichloro)] pentaisocyanurate and (mono-trichloro) (monopotassium dichloro) di-isocyanurate is achieved at pH values maintained from 3.5 to 4.0 and at temperatures of 45° to 60° C.

The reaction pH must be maintained during the course of the reaction within these pH values to obtain the noted products. This is achieved by employing any organic or mineral acid which is compatable with the system, that is an acid that does not react with the starting compounds or resulting complexes. Preferred mineral acids include sulfuric acid, hydrochloric acid, phosphoric acid, nitric acid, and perchloric acid. Preferred organic acids include acetic acid and propionic acid.

Reaction between the unsubstituted or amino substituted triazines and potassium hypochlorite is extremely rapid under operating conditions with complete conversions being achieved in a matter of minutes. There is, however, a competing reaction causing triazine ring breakdown, which reaction occurs at a slightly slower rate. In order to maximize conversion of the triazines into [(mono-trichloro) tetra-(monopotassium dichloro)] penta-isocyanurate while minimizing triazine ring rupture, the reaction is carried out in less than about 5 minutes and preferably in less than about 2 minutes. These reaction times can be achieved by employing conventional reactors. Reaction times of up to 90 seconds are feasible with commercially available pipe reactors. A pipe reactor is an elongated tubular reaction chamber wherein the feed enters the reactor in one end and product exits out the other end. The reaction takes place within the tube which is heated by external sources. Use of pipe reactors greatly increases the production of the potassium containing chloroisocyanurate complexes of this invention and eliminates the need for larger type reactors.

Mixing of the unsubstituted or amino substituted triazine and potassium hypochlorite to form the resulting slurry as well as heating the aqueous medium are achieved by conventional means and procedures. Mixing and heating may be done separately or carried out in a single stage. Since this is an exothermic reaction, temperature control of the aqueous reaction medium is easily achieved by conventional external cooling means. The reaction is then permitted to go to completion.

When the reaction is complete, the aqueous solution is cooled by conventional means to precipitate the potassium-containing chloroisocyanurate complexes. Preferably, the reaction solution is rapidly cooled in less than about 10 minutes to below about 20° and preferably to below about 10° C. Cooling is essential to prevent triazine losses due by ring rupture and to lower the solubility of the complexes in the reaction medium. The precipitated crystals are removed from the solution by any conventional liquid-solid separatory means.

The recovered crystals may then be optionally dried and stored. Drying may be carried out in any conventional manner to remove residual moisture and to produce a free-flowing crystalline product. These procedures are well known in the art and do not constitute a part of the invention.

The invention will be better understood from a consideration of the following examples. The examples are given to illustrate the invention, and are not deemed to be limiting thereof. All percentages given are based on weight unless otherwise indicated.

EXAMPLE I

Production of [(mono-trichloro) tetra-(monopotassium dichloro)] penta-isocyanurate A 7.65 gram (0.0593 mole) sample of crude cyanuric acid prepared from urea assaying 80% cyanuric acid, 17% ammelide and 3% ammeline was added to 102.4 grams of an aqueous solution containing 19 grams potassium hypochlorite. This addition took place in less than two seconds. The aqueous solution had a pH value of 10.5 and a temperature of 35° C. The reaction temperature rose to 55° C and was maintained at 55° C for 2 minutes. The pH value of the reaction mixture was initially adjusted to and maintained at 4.9 with acetic acid during the course of the reaction. The reaction vessel was then quenched in an ice bath and the reaction solution rapidly cooled to 15° C within two minutes. A white solid precipitate was removed from the slurry, washed and dried at 120° C under 20 mm Hg pressure. The precipitate was pure [(mono-trichloro) tetra-(monopotassium dichloro)] penta-isocyanurate analyzing 66.3% available chlorine. The total yield was 12.1 grams which is equivalent to 87% recovery based on starting triazines.

EXAMPLE II

Production of complex mixtures containing [(mono-trichloro) tetra-(monopotassium dichloro)] penta-isocyanurate and (mono-trichloro) (monopotassium dichloro) di-isocyanurate A 7.65 gram (0.0593 mole) sample of crude cyanuric acid prepared from urea assaying 78.9% cyanuric acid, 17.6% ammelide, 3.4% ammeline and 0.1% melamine was added to 97.4 grams of an aqueous solution containing 13.6 grams potassium hypochlorite. This addition took place in less than two seconds. The aqueous solution had a pH value of 10.5 and a temperature of 35° C. The reaction temperature rose to 55° C and was maintained between 55° and 60° C for two minutes. The pH value of the reaction mixture was initially adjusted to and maintained at 3.7 with 9 grams glacial acetic acid and 3 grams of 50% sulfuric acid during the course of the reaction. The reaction vessel was then quenched in an ice bath and the reaction solution rapidly cooled to 15° C within two minutes. A white solid precipitate was removed from the slurry, washed and dried at 130° C under 20 mm Hg pressure. The precipitate was a mixture of crystalline [(mono-trichloro) tetra-(monopotassium dichloro)] pentaisocyanurate and (mono-trichloro) (monopotassium dichloro) di-isocyanurate analyzing 70.1% available chlorine. The total yield was 6.6 grams which is equivalent to 86% recovery based on starting triazines.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A process for preparing crystalline [(mono-trichloro) tetra-(monopotassium dichloro)] penta-isocyanurate and mixtures containing the same, which comprises:

reacting an unsubstituted or amino substituted triazine selected from the group consisting of purified cyanuric acid, melamine, ammeline, ammelide, ammeline:ammelide complex, cyanuric acid:melamine complex, crude cyanuric acid, and mixtures thereof with at least stoichiometric amounts of potassium hypochlorite in an aqueous medium at a temperature of 35° to 70° C, and at a pH value of 3.2 to 5.7 for less than about five minutes to completely N-chlorinate all of the available sites on the triazine molecule that can be N-chlorinated and to remove any N,N-dichloro exocyclic nitrogens;

cooling the reaction medium to precipitate [(monotrichloro) tetra-(monopotassium dichloro)] penta-isocyanurate; and recovering crystalline [(mono-trichloro) tetra-(monopotassium dichloro)] penta-isocyanurate.

2. The process of claim 1 wherein the aqueous medium contains 3 to 20 weight percent of the amino substituted triazine based on the weight of the reaction solution.

3. The process of claim 1 wherein the aqueous medium contains 6 to 14 weight percent of the amino substituted triazine based on the weight of the reaction solution.

4. The process of claim 1 wherein the reaction medium is maintained at a pH value between 4.0 and 5.5.

5. The process of claim 1 wherein the reaction medium is maintained at a pH value between 3.5 and 4.0 and the precipitate is a mixture of crystalline [(mono-trichloro) tetra-(monopotassium dichloro)] penta-isocyanurate and crystalline (mono-trichloro) (monopotassium dichloro) di-isocyanurate.

6. The process of claim 1 wherein the reaction temperature is maintained between 45° and 65° C.

7. The process of claim 1 wherein the reaction solution is rapidly cooled to below and about 20° C to precipitate the potassium-containing chloroisocyanurate complex.

8. A process for preparing [(mono-trichloro) tetra-(monopotassium dichloro)] penta-isocyanurate, which comprises:

mixing sufficient amounts of an unsubstituted or amino substituted triazine selected from the group consisting of purified cyanuric acid, melamine, ammeline, ammelide, ammeline:ammelide complex, cyanuric acid:melamine complex, crude cyanuric acid, and mixtures thereof, with potassium hypochlorite in an aqueous medium to form a 6 to 14 weight percent unsubstituted or amino substituted triazine slurry based on the weight of the solution, said potassium hypochlorite being employed in amounts of at least 10% above the stoichiometric amount necessary to completely N-chlorinate all of the available sites on the triazine molecule that can be N-chlorinated and to remove any N,N-dichloro exocyclic nitrogens;

reacting the slurry at a temperature from 45° C to 60° C at a pH value from 4.0 to 5.5 for less than about five minutes;

cooling the slurry to below about 20° C to precipitate crystalline [(mono-trichloro) tetra-(monopotassium dichloro)] penta-isocyanurate; and recovering the crystalline [(mono-trichloro) tetra-(monopotassium dichloro)] penta-isocyanurate.

9. The process of claim 8 wherein the reaction medium is maintained at a pH value between 4.7 and 5.0.

10. A process for preparing a mixture comprising [(mono-trichloro) tetra-(monopotassium dichloro)] penta-isocyanurate, and (mono-trichloro) (monopotassium dichloro) di-isocyanurate which comprises:

mixing sufficient amounts of an unsubstituted or amino substituted triazine selected from the group consisting of purified cyanuric acid, melamine, ammeline, ammelide, ammeline:ammelide complex, cyanuric acid:melamine complex, crude cyanuric acid, and mixtures thereof, with potassium hypochlorite in an aqueous medium to form a 6 to 14 weight percent unsubstituted or amino substituted triazine slurry based on the weight of the solution, said potassium hypochlorite being employed in amounts of at least 10% above the stoichiometric amount necessary to completely N-chlorinate all of the available sites on the triazine molecule that can be N-chlorinated and to remove any N,N-dichloro exocyclic nitrogens;

reacting the slurry at a temperature from 45° to 60° C at a pH value from 3.5 to 4.0 for less than about five minutes;

cooling the slurry to below about 20° C to precipitate a crystalline complex mixture of [(mono-trichloro) tetra-(monopotassium dichloro)] penta-isocyanurate and (mono-trichloro) (monopotassium dichloro) di-isocyanurate; and recovering a crystalline complex mixture of [(mono-trichloro) tetra-(monopotassium dichloro)] penta-isocyanurate and (mono-trichloro) (monopotassium dichloro) di-isocyanurate.

* * * * *